US005739030A

United States Patent [19]
Ward

[11] Patent Number: 5,739,030
[45] Date of Patent: Apr. 14, 1998

[54] PRODUCTION OF FOOD

[75] Inventor: Philip Nigel Ward, Darlington, United Kingdom

[73] Assignee: Zeneca Limited, London, England

[21] Appl. No.: 696,821

[22] PCT Filed: Feb. 22, 1995

[86] PCT No.: PCT/GB95/00368

§ 371 Date: Aug. 20, 1996

§ 102(e) Date: Aug. 20, 1996

[87] PCT Pub. No.: WO95/23843

PCT Pub. Date: Sep. 8, 1995

[30] Foreign Application Priority Data

Mar. 1, 1994 [GB] United Kingdom .................. 9403930

[51] Int. Cl.$^6$ .................................................. C12N 1/14

[52] U.S. Cl. .................................................. 435/256.5

[58] Field of Search ............................ 435/68, 71.1, 929, 435/256.5, 220, 254, 254.1; 530/371; 514/2

[56] References Cited

U.S. PATENT DOCUMENTS

| | | | |
|---|---|---|---|
| 4,163,692 | 8/1979 | Yates | 435/256.5 |
| 4,501,765 | 2/1985 | Towersey et al. | 426/656 |
| 4,555,485 | 11/1985 | Marsh | 435/71.1 |

FOREIGN PATENT DOCUMENTS

| | | |
|---|---|---|
| 1 440 642 | 6/1976 | United Kingdom . |
| 91/17669 | 11/1991 | WIPO . |

OTHER PUBLICATIONS

Ohta, S. et al. 1971 Applied Microbiology 22(3): 415–421.
Maul, S.B. et al. 1970 Nature 228 (181).

*Primary Examiner*—James Ketter
*Assistant Examiner*—Irem Yucel
*Attorney, Agent, or Firm*—Pillsbury Madison & Sutro LLP

[57] ABSTRACT

The RNA content of Fungi Imperfecti, for example *Fusarium graminearum* can be reduced with low protein loss by heating it in the presence of its growth medium to a temperature above 68° C. and separating growth medium from it.

10 Claims, No Drawings

PRODUCTION OF FOOD

This application claims benefit of international application PCT/GB9500368, filed Feb. 22, 1995.

THIS INVENTION relates to the production of food.

It is known to produce food suitable for consumption by humans by culturing fungi. Suitable fungi are microfungi of the class Fungi Imperfectio A process of this type is described in British Patents Nos. 1,210,356 and 1,346,062 and strains of Fusarium for use in food production are described in British Patent 1,346,061 and in U.S. Pat. No. 4,347.

In order to render such products more suitable for consumption by humans it is considered desirable to reduce their nucleic acid content. British Patent No 1,440,642 discloses a process in which this is achieved by subjecting Fungi Imperfecti to a temperature of 55° to 72° C. for a period of at least 60 seconds at a pH of 4.7 to 7.0. This temperature was apparently selected because ribonuclease survives such conditions whereas protease is destroyed; thus the protein content of the fungus would not be degraded by protease but the ribonucleic acid would be degraded by the ribonuclease. The process is disclosed as producing a final RNA content of 1 to 4% from organisms originally containing 7 to 12%. In certain instances RNA contents of the product of less than 1% were disclosed. In the experiments described fungi were generally separated from their growth media and heated in the presence of water or aqueous solutions of NaCl or $NH_4Cl$ under various conditions. In example J however the fungi were heated in the presence of their growth medium to a temperature of 64° C., filtered, washed, reslurried in water and spray dried.

The effect of temperature and duration of heat treatment is shown in Example A of British Patent No 1,440,642. In no case of treatment above 66° C. was the final RNA content below the 2% by weight level, which figure was not corrected for biomass loss. The figure based on the final product after biomass loss would have been higher.

The above process suffers considerable loss of proteinaceous material however.

We have now devised a process in which any loss of ribonuclease activity does not prevent a satisfactory reduction in nucleic acid content.

We have now found that it is possible to carry out effective removal of RNA with less loss of protein by operating at higher temperatures in the range of over 68° C. to 80° C., preferably 69° to 75° C. and more preferably 70° to 74° C. for example above 72° up to 74° C. providing that the fungus is raised to such temperatures in the presence of its growth medium.

It is not known why this phenomenon occurs, but it may be that the fungus in its growing state is more susceptible to RNA loss on heating and that maintaining it in contact with its growth medium to the treatment temperature maintains it in its susceptible state.

The invention comprises a process in which the nucleic acid content of Fungi Imperfecti is reduced which comprises growing it in the presence of a growth medium, raising its temperature in the presence of the growth medium to above 68° C. and preferably at most 80° C. for example 69° to 75° C., preferably 70° to 74° C. and more preferably above 72° C. to 74° C. and separating at least part of the growth medium from the fungus. Nucleic acid passes from the fungus to the growth medium and the treated fungus has a reduced nucleic acid content.

The process permits a high retention of fungal components of nutritional value especially protein. It is believed that protein is retained more readily because during nucleic acid removal it is in a substantially coagulated state. At temperatures higher than 80° C. the coagulation of proteinaceous material can occur sufficiently rapidly to impede adequate loss of nucleic acids and at temperatures lower than 68° C. it is generally insufficient to prevent a substantial loss of protein.

The nucleic acid content of the treated fungus is preferably at most 3% or more preferably at most 2% by weight, for example about 1% by weight.

The fungus is suitably an edible strain of Fusarium, for example *Fusarium graminearium, Fusarium oxysporum* or *Fusarium solani*. *Fusarium graminearium* Schwabe IMI 145 425 deposited with the Commonwealth Agricultural Bureau, International Mycological Institute (IMI), Ferry Lane, Kew, Surrey, TW9 3AF on 26 Feb. 1970 and 3 Feb. 1979, has been approved for use in foodstuffs by the regulatory authorities in UK and may be treated by this invention.

The process may be carried out under a wide range of conditions. The pH and constitution of the growth medium should be such that growth of the fungus in it can occur at normal temperatures but if desired it can be modified in the process; for example if heating takes place by steam injection the steam may contain an acidic or alkaline gas, for example $SO_2$ or $NH_3$. A pH during the nucleic acid removal of 4 to 8, preferably 4.5 to 7 and more preferably 5 to 6.5 is however desirable. Rapid heating from the growth temperature (which is normally below about 30° C. for example 28° C.) to the nucleic acid removal temperature is preferred. Suitably such heating should be rapid, preferably taking less than five seconds, more preferably less than one second.

The product may be washed to remove residual nucleic acids in adhering growth medium but this is not essential if most of the growth medium is removed for example by drainage or filtration.

EXAMPLE

*Fusarium Graminearum* IMI 145,425 was grown in a continuous fermenter at 28° C. in the presence of a growth medium of the following composition at a dilution rate of 0.16 to 0.23/h maintaining a dry cell weight of 14.5 g/kg in the fermenter, and with continuous aeration with sterile air containing ammonia gas.

|  | Steady Operation | Operating Limits |
|---|---|---|
| Iron | <0.05 ppm | <0.05–0.10 ppm |
| Calcium | 45 ppm | 35–55 ppm |
| Phosphorus | 300 ppm | 200–400 ppm |
| Magnesium | 60 ppm | 40–80 ppm |
| Potassium | 600 ppm | 400–800 ppm |
| Manganese | 0.6 ppm | 0.2–1.0 ppm |
| Zinc | 0.5 ppm | 0.3–0.7 ppm |
| Copper | 0.12 ppm | 0.08–0.16 ppm |
| Glucose | — | 1–5 g/kg |

The pH was controlled at 6 by the continuous addition of ammonia gas. The phosphorous was supplied as phosphoric acid, the calcium as the acetate and other salts as the sulphates.

Culture at 28° C. is passed into a Continuous Stirred Tank Reactor (CSTR) with the temperature maintained at the temperature shown in the tables below by direct steam injection. The culture is then maintained at this temperature in the tank for a mean residence time of 30 to 45 minutes. The output from the tank was fed to a belt filter from which a wet product containing greater than 20% total solids is removed, as assessed by drying for 24 hours at 105° C. It has a nucleic acid content of less than 2% on a dry weight basis as seen from the following tables of results. No washing was carried out. The process was continuous and samples were taken daily. Two production runs were carried out and the results are presented in the following tables. The data at the end of each 24 hour period are recorded vertically and sequentially in the tables.

Run 1

| Temp. [°C.] | Final Nucleic acid [%]+ | Temp. [°C.] | Final Nucleic acid [%]+ | Temp. [°C.] | Final Nucleic acid [%]+ |
|---|---|---|---|---|---|
| 72.6 | 1.5 | 72.5 | 1.0 | 74.0 | 0.9 |
| 72.6 | 1.3 | 73.3 | 1.1 | 71.9 | 1.0 |
| 73.1 | 1.1 | 72.3 | 1.1 | 72.7 | 1.0 |
| 71.4 | 1.0 | 72.5 | 1.2 | 72.0 | 1.0 |
| 71.7 | 1.7* | 72.6 | 1.2 | 72.9 | 0.9 |
| 73.0 | 1.3 | 72.3 | 1.2 | 73.7 | 0.9 |
| 73.2 | 1.2 | 73.4 | 1.1 | 72.0 | 1.1 |
| 73.0 | 1.0 | 72.3 | 1.2 | 73.0 | 1.0 |
| 73.0 | 1.1 | 73.0 | 1.0 | 73.1 | 1.0 |
| 74.1 | 1.3 | 74.0 | 1.0 | 72.3 | 1.2 |

Data marked * is considered to be erroneous - Experimental error.

Run 2

| Temp. [°C.] | Final Nucleic acid [%]+ | Temp. [°C.] | Final Nucleic acid [%]+ | Temp. [°C.] | Final Nucleic acid [%]+ |
|---|---|---|---|---|---|
| 72.5 | 1.3 | 64.0 | 0.6 | 74.0 | 1.2 |
| 73.0 | 1.0 | 64.3 | 0.7 | 72.8 | 1.3 |
| 71.7 | 1.3 | 70.2 | 1.1 | 73.3 | 1.4 |
| 72.6 | 1.4 | 73.3 | 1.1 | 73.1 | 1.1 |
| 72.3 | 1.4 | 72.1 | 1.3 | 73.4 | 1.1 |
| 73.4 | 1.4 | 73.7 | 1.5 | 73.5 | 1.0 |
| 72.7 | 1.3 | 73.5 | 1.4 | 70.7 | 0.9 |
| 72.4 | 1.2 | 72.7 | 1.3 | 73.1 | 1.2 |
| 63.8 | 0.7 | 72.9 | 0.8 | 72.6 | 0.9 |

+By weight based on total dry matter

The example below, from plant trial, shows the influence of nucleic acid removal at 73.25° C. and 64° C. on biomass loss. A clear fall is seen after the reduction temperature is increased. The data are recorded hourly. It is believed that the first result after reducing the temperature to 64° C. was influenced by the carry-over of material processed at 73¼° C.

| Nucleic Acid Removal temp. [°C.] | Fermenter Output, Dry-cell weight | Dry cell weight after Nucleic Acid removal** | Biomass loss on Nucleic Acid Removal % | Final Nucleic Acid % |
|---|---|---|---|---|
| 64 | *15.25 | 9.5 | 37.7 | 0.8 |
| 64 | 15 | 9.7 | 35.3 | 0.8 |
| 73¼ | *15.1 | 10.2 | 32.6 | 0.9 |
| 73¼ | 15.2 | 10.1 | 33.7 | 1.2 |
| 73¼ | *15.35 | 10.7 | 30.5 | 1.1 |
| 73¼ | 15.5 | 9.5 | 38.8# | 1.2 |
| 64 | *15.45 | 10.4 | 32.7 | 1.0 |
| 64 | 15.4 | 9.7 | 37.0 | 0.8 |

Note:
*Dry cell weight calculated as the average of those either side. The dry cell weight was measured every two hours.
Believed high due to analytical/sampling error or recording error.
**Corrected for steam dilution. At 64° C. 60.2 of bar g steam per kg culture is required for heating. At 73.25° C. (the average logged temperature during the trial) 75.33 of 4 bar g steam per kg culture is required. To allow for this the reduced culture dry weights are multiplied by 1.0602 and 1.0754 respectively, before calculating biomass losses.

I claim:

1. A process in which the nucleic acid content of Fungus Imperfectus is reduced to less than 2% by weight which comprises growing the fungus in the presence of a growth medium, raising the temperature of the growth medium while the fungus is still growing in the presence of the growth medium to above 68° C. and then separating at least part of the growth medium from the fungus whereby the nucleic acid content of said fungus is reduced while minimizing the loss of protein.

2. A process as claimed in claim 1 in which the temperature of the growth medium is raised to a temperature in the range above 72° C. and at most 74° C.

3. A process as claimed in claim 1 in which the fungus is an edible strain of Fusarium.

4. A process as claimed in claim 3 in which the fungus is *Fusarium graminearum*.

5. A process as claimed in claim 1 in which the pH of the growth medium is 4.5 to 7.

6. A process as claimed in claim 1 in which the temperature of the growth medium is raised from the growth temperature to the nucleic acid removal temperature in less than five seconds.

7. A process as claimed in claim 1 in which the fungus and growth medium are heated by steam injection.

8. A process as claimed in claim 6 in which a pH modifying gas is present in the steam.

9. A process as claimed in claim 7 in which the fungus and growth medium at substantially growth temperature are passed into a vessel containing liquid at above 68° C.

10. A process as claimed in claim 9, wherein the liquid is at a temperature above 72° C.

* * * * *